(12) United States Patent
Clifford et al.

(10) Patent No.: US 7,191,916 B2
(45) Date of Patent: Mar. 20, 2007

(54) DEVICE FOR DISPENSING FLUID MEDICINE

(75) Inventors: Julia A. Clifford, Arlington, TX (US); William E. McCune, Fort Worth, TX (US); Robert W. Ashlin, Jr., Holly Lake Ranch, TX (US); David W. Lennox, Saegertown, PA (US)

(73) Assignee: Alcon, Inc., Hunenberg (CH)

( * ) Notice: Subject to any disclaimer, the term of this patent is extended or adjusted under 35 U.S.C. 154(b) by 93 days.

(21) Appl. No.: 10/979,686

(22) Filed: Nov. 2, 2004

(65) Prior Publication Data

US 2005/0133543 A1 Jun. 23, 2005

Related U.S. Application Data

(63) Continuation of application No. 10/782,686, filed on Feb. 19, 2004, now Pat. No. 6,814,265.

(60) Provisional application No. 60/452,372, filed on Mar. 6, 2003.

(51) Int. Cl.
*B67D 5/06* (2006.01)

(52) U.S. Cl. .................... 222/23; 222/214; 222/420; 222/631; 222/641; 222/182

(58) Field of Classification Search ................ 222/63, 222/420, 641–642, 182–183, 324–325, 630–631, 222/472, 474, 105, 23, 26, 212–215; 604/294–301, 604/890.1, 66
See application file for complete search history.

(56) References Cited

U.S. PATENT DOCUMENTS

| | | | |
|---|---|---|---|
| 1,775,400 A | 9/1930 | Kramer | |
| 4,543,096 A | 9/1985 | Keene | |
| 4,678,105 A | 7/1987 | Heck | |
| 4,973,322 A | 11/1990 | Jewart | |
| 5,133,702 A | 7/1992 | Py | |
| 5,347,453 A | 9/1994 | Maestre | |
| 5,387,202 A | 2/1995 | Baron | |
| 5,401,259 A | 3/1995 | Py | |
| 5,495,961 A | 3/1996 | Maestre | |
| D368,774 S | 4/1996 | Py | |
| 5,578,020 A | 11/1996 | Mosley | |
| 5,624,057 A | 4/1997 | Lifshey | |
| 5,702,032 A * | 12/1997 | Loehrke | ............ 222/63 |
| D413,668 S | 9/1999 | Mannberg et al. | |
| 6,107,911 A | 8/2000 | Perrone | |
| D444,874 S | 7/2001 | Haffner et al. | |
| D445,177 S | 7/2001 | Cogger | |
| D446,739 S | 8/2001 | Kan | |
| D446,740 S | 8/2001 | Cruitt | |

(Continued)

FOREIGN PATENT DOCUMENTS

EP  0 335 513  3/1989

(Continued)

OTHER PUBLICATIONS

JPO/PAJ/MicroPatent Abstract for Japanese Patent Application No. 10211254.

(Continued)

*Primary Examiner*—Frederick C. Nicolas
(74) *Attorney, Agent, or Firm*—W. David Lee

(57) ABSTRACT

A dispensing device for fluid medicine includes a housing having an opening leading to an interior and a plastic dropper bottle at least partially disposed in the interior through the opening. The bottle has a container holding fluid medicine to be dispensed and a nozzle with an aperture in fluid communication with the container. The device may include a tilt switch, a closure switch, and other electronics that improve patient compliance.

2 Claims, 6 Drawing Sheets

U.S. PATENT DOCUMENTS

| | | | |
|---|---|---|---|
| D447,074 S | 8/2001 | Chan | |
| 6,354,468 B1 * | 3/2002 | Riek | 222/129.3 |
| 6,423,040 B1 | 7/2002 | Benktzon et al. | |
| 6,506,183 B2 | 1/2003 | Cogger | |
| 6,524,287 B1 | 2/2003 | Cogger | |
| 6,814,265 B2 | 11/2004 | Clifford et al. | |
| 6,869,413 B2 * | 3/2005 | Langley et al. | 604/65 |
| 6,942,646 B2 * | 9/2005 | Langley et al. | 604/207 |
| 6,997,906 B2 * | 2/2006 | Langley et al. | 604/151 |

FOREIGN PATENT DOCUMENTS

| | | |
|---|---|---|
| GB | WO02051475 A1 * | 7/2002 |
| WO | WO 02/085282 | 10/2002 |
| WO | WO 04/013009 | 2/2004 |

OTHER PUBLICATIONS

JPO/PAJ/MicroPatent Abstract for Japanese Patent Application No. 09056777.

JPO/PAJ/MicroPatent Abstract for Japanese Patent Application No. 2001120639.

JPO/PAJ/MicroPatent Abstract for Japanese Patent Application No. 04082553.

JPO/PAJ/MicroPatent Abstract for Japanese Patent Application No. 2000126272.

JPO/PAJ/MicroPatent Abstract for Japanese Patent Application No. 2000116748.

JPO/PAJ/MicroPatent Abstract for Japanese Patent Application 11076366.

JPO/PAJ/MicroPatent Abstract for Japanese Application No. 2001120638.

JPO/PAJ/MicroPatent Abstract for japanese Patent Application No. 11276548.

PCT/MicroPatent Abstract for European Application No. 335513.

PCT/MicroPatent Abstract for European Application No. 576649.

PCT/MicroPatent Abstract for PCT Application No. 9509669.

Pharpack Europe; Nov. 2002; No. 5: "Valois: Thinking Lateral with Nasal Devices" p. 15.

ARLT: ALR Technologies, Inc.; News article "ALR Technologies Announces Reminder Response System Development" Jun. 17, 2002, 2 pgs.

DIALOG (R) File 583: Gale Group Globalbase (TM) (c) 2002 The Gale Group, "Allergen Launches Compliance Cap", 1 pg.

2003 PJB Publications Ltd., Newsletter regarding "Allergen Compliance Cap", 1 pg.

Pharpack Europe; November 2002; No. 5; "Smart Packages May Help Control Prescriptions" p. 30.

* cited by examiner

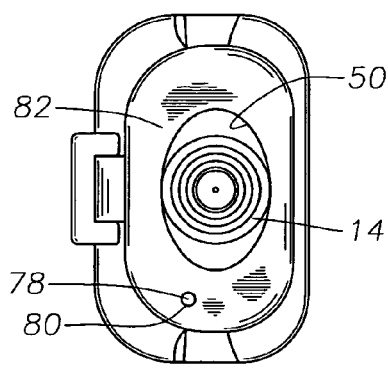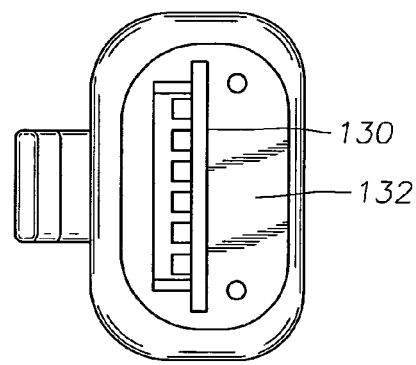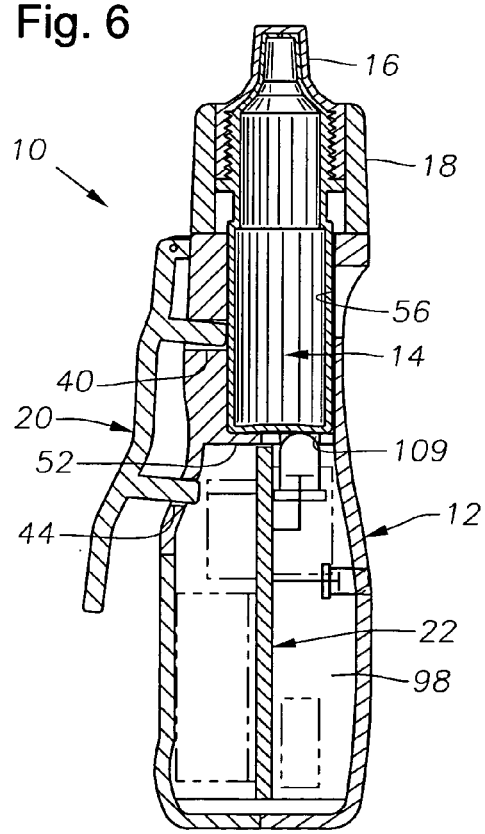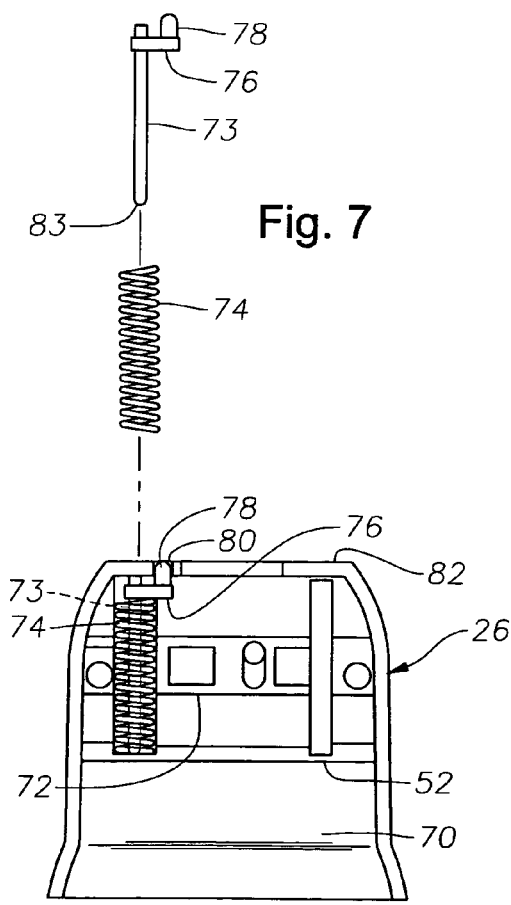

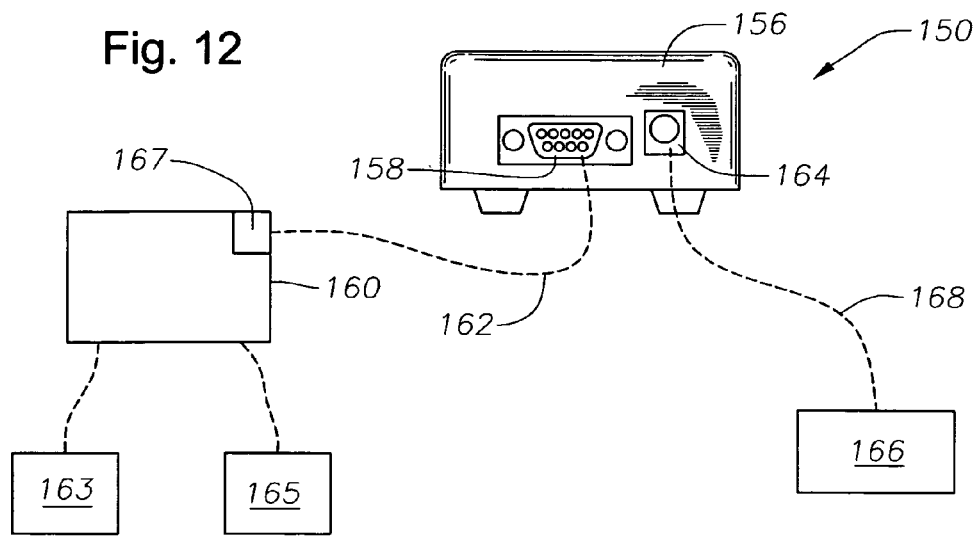

| DropLog | | | |
|---|---|---|---|
| PatientSS | Date | Time | No.Drops |
| 202110 | 02/21/2002 | 7:02:00 PM | 4 |
| 202110 | 02/22/2002 | 7:06:00 PM | 1 |
| 202110 | 02/23/2002 | 7:05:00 PM | 1 |
| 202110 | 02/24/2002 | 10:03:00 PM | 4 |
| 202110 | 02/25/2002 | 5:06:00 PM | 1 |
| 202110 | 02/26/2002 | 9:05:00 PM | 1 |
| 202110 | 02/27/2002 | 5:01:00 PM | 1 |
| 202110 | 02/28/2002 | 8:06:00 PM | 1 |
| 202110 | 03/01/2002 | 8:04:00 PM | 3 |
| 202110 | 03/02/2002 | 8:05:00 PM | 3 |
| 202110 | 03/03/2002 | 8:03:00 PM | 3 |
| 202110 | 03/04/2002 | 10:05:00 PM | 4 |
| 202110 | 03/05/2002 | 7:06:00 PM | 1 |
| 202110 | 03/06/2002 | 9:05:00 PM | 2 |

_US 7,191,916 B2_

DEVICE FOR DISPENSING FLUID MEDICINE

This application is a continuation of U.S. application Ser. No. 10/782,686, filed Feb. 19, 2004, now U.S. Pat. No. 6,814,265, which claims priority from U.S. Provisional Application No. 60/452,372 filed Mar. 6, 2003.

FIELD OF THE INVENTION

The present invention generally pertains to devices for dispensing fluid medicines. The present invention more particularly pertains to such devices that are designed to increase the ease with which a patient may dispense medicine and to increase patient compliance with dosing instructions for the medicine.

DESCRIPTION OF THE RELATED ART

Ease of dispensing fluid medicines and compliance with dosing instructions are primary concerns with all patients. In particular, elderly patients, or other patients lacking sufficient strength and/or dexterity in their hands, often experience problems dispensing medicine from the small, plastic dropper bottles typically used for fluid medicines. In addition, all patients, including elderly patients, sometimes forget to take their medicine at the appropriate interval as prescribed by their physicians. Furthermore, physicians must typically rely upon their patients to comply with the dosing regimen for a medicine. Any feedback received by a physician regarding compliance typically comes from the patient, as well. While important for all medicines, the above concerns become increasingly important for medicines where repetitive, frequent administration are required, such as medicines for the treatment of ophthalmic conditions such as glaucoma.

The literature reveals several devices that attempt to address certain of these issues. A plastic casing that receives a conventional plastic eye dropper bottle and has sufficient flexibility to allow a user to squeeze the bottle and dispense a drop by squeezing the outside surface of the casing has been marketed in the United Kingdom under the name Opticare®. The casing provides a greater surface area for the patient to hold the bottle and thus helps patients with minimal dexterity who experience difficulty holding and manipulating small bottles. European Patent No. 0335513 discloses a holder for a plastic eye dropper bottle having dual handles that help patients with minimal strength in their hands to squeeze the bottle and dispense solution. However, the handles of this holder create portability and storage issues and are somewhat awkward in appearance. U.S. Pat. No. 6,423,040 to Benktzon et al. discloses an eye fluid applicator having a pumping mechanism with a button pushed by the user to dispense medicine. U.S. Pat. Nos. 5,347,453 and 5,495,961 to Maestre and U.S. Pat. No. 6,107,911 to Perrone disclose portable devices for holding an eye dropper bottle that can be programmed to notify the patient of the time for taking medication.

Despite these attempts, a need still exists for an improved device for dispensing fluid medicines that addresses all the above-described physiological and compliance concerns, maximizes patient safety and ease of use, and does not suffer from the limitations of existing devices.

SUMMARY OF THE INVENTION

The present invention is directed to a dispensing device for fluid medicine. The device includes a housing having an opening leading to an interior. The device also includes a plastic dropper bottle at least partially disposed in the interior through the opening. The bottle has a container holding fluid medicine to be dispensed and a nozzle with an aperture in fluid communication with the container.

In one aspect of the present invention, the device includes a printed circuit board disposed within the housing. The printed circuit board has a microcontroller and a switch in electrical communication with the microcontroller. The switch is capable of signaling the microcontroller when the device is oriented by a user so that the container is disposed generally above the nozzle.

In another aspect of the present invention, the device includes a closure, and a printed circuit board disposed within the housing. The printed circuit board has a microcontroller and a switch in electrical communication with the microcontroller. The switch is capable of sensing whether the closure is disposed on the device. The microcontroller activates a medicine dispensing recording mode of the device when the switch signals the microcontroller that the closure is not disposed on the device.

BRIEF DESCRIPTION OF THE DRAWINGS

For a more complete understanding of the present invention, and for further objects and advantages thereof, reference is made to the following description taken in conjunction with the accompanying drawings in which:

FIG. 4 shows a top view of the device of FIG. 1;

FIG. 5 shows a bottom view of the device of FIG. 1;

FIG. 6 shows a side, sectional view of the device of FIG. 1;

FIG. 7 shows an internal, partially exploded view of an upper rear housing of the device of FIG. 1;

FIG. 12 shows a rear view of the cradle of FIG. 10;

FIG. 13 shows an exemplary computer screen utilized to program the device of FIG. 1.

DETAILED DESCRIPTION OF THE PREFERRED EMBODIMENTS

Figure 1:
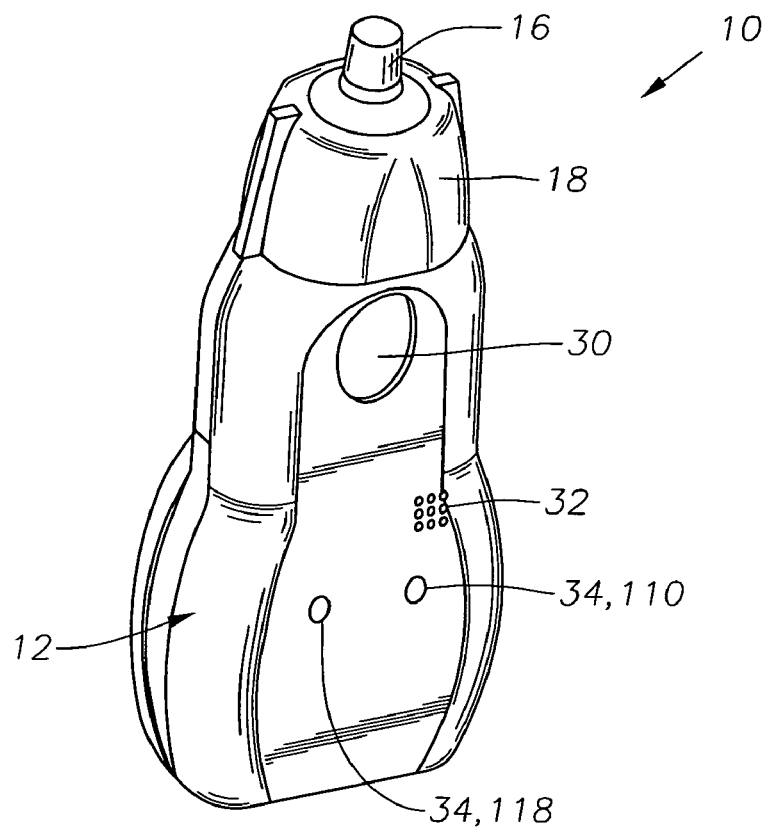
FIG. 1 shows a front, perspective view of a device for dispensing fluid medicine according to a preferred embodiment of the present invention.
Figure 2:
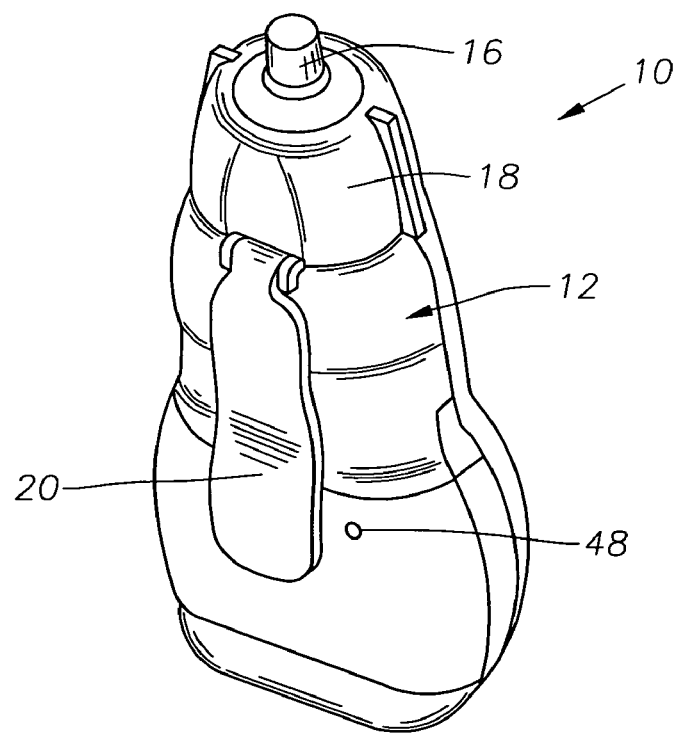
FIG. 2 shows a rear, perspective view of the device of FIG. 1.
Figure 3:
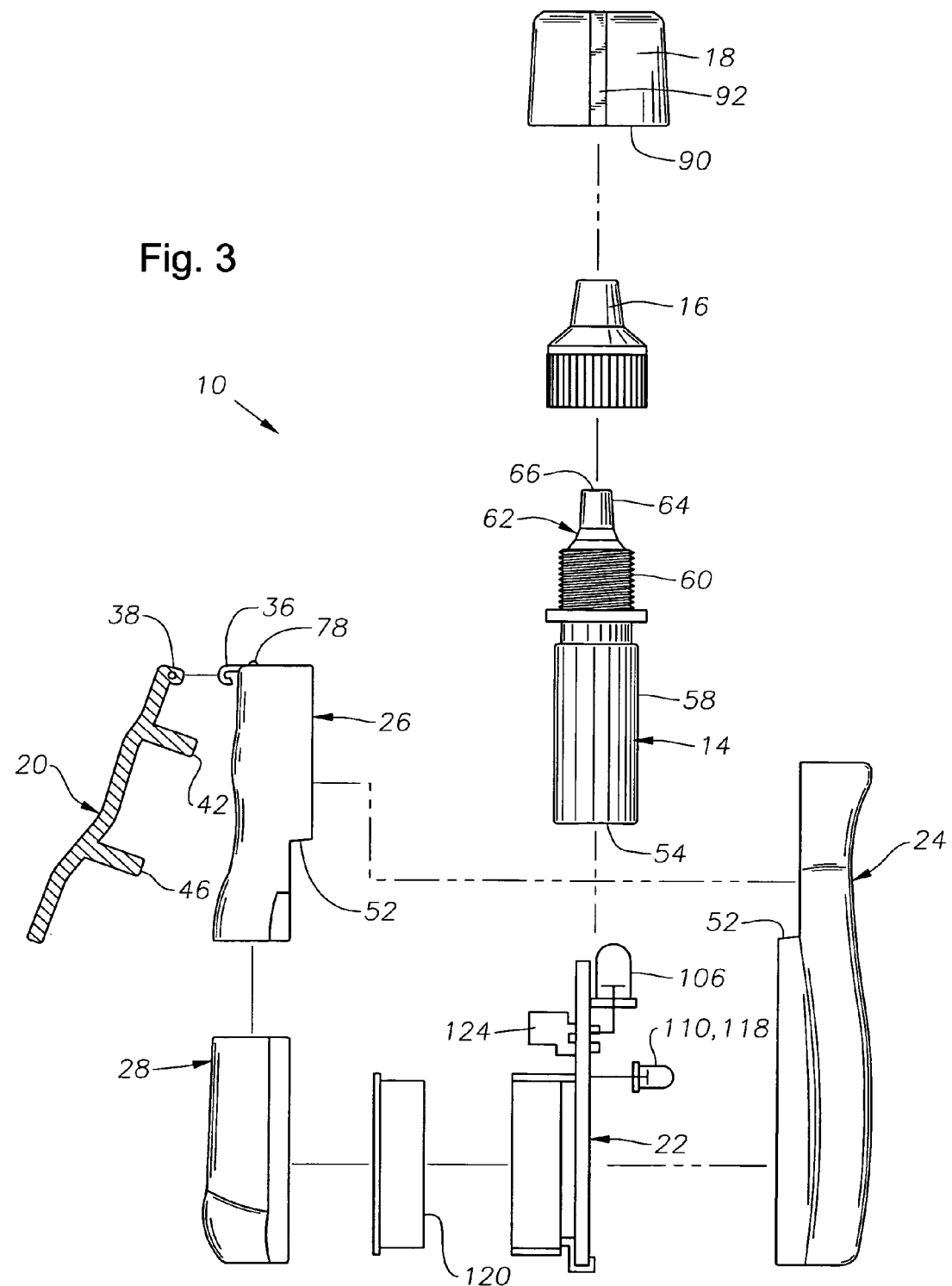
FIG. 3 shows a side, exploded view of the device of FIG. 1.
Figure 8:
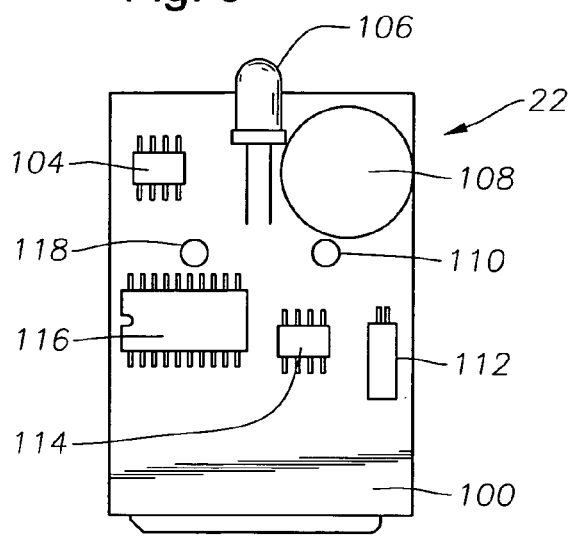
FIG. 8 shows a front view of the printed circuit board of the device of FIG. 1.
Figure 9:
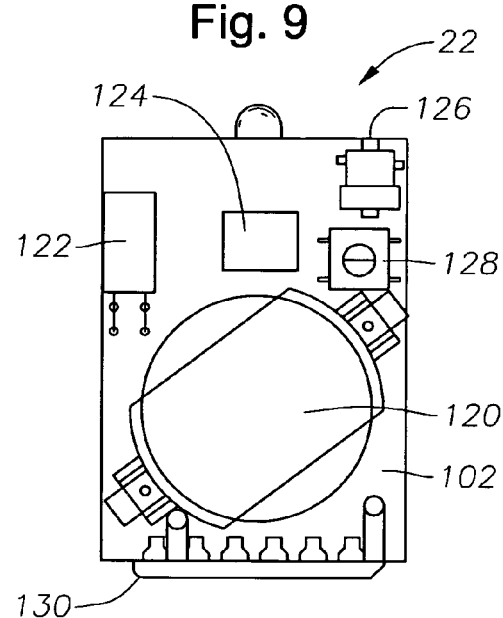
FIG. 9 shows a rear view of the printed circuit board of FIG. 8.

The preferred embodiments of the present invention and their advantages are best understood by referring to FIGS. 1–15 of the drawings, like numerals being used for like and corresponding parts of the various drawings.

FIGS. 1–9 show a device 10 for dispensing a fluid medicine according to a preferred embodiment of the present invention. Device 10 generally includes a housing 12, a plastic dropper bottle 14 that contains the fluid medicine to be dispensed and that is partially received within housing 12, a dropper bottle closure 16, a device closure 18, a lever 20, and a printed circuit board 22.

Housing 12 preferably includes a front housing 24, an upper rear housing 26, and a lower rear housing 28. Front housing 24 includes an opening 30 providing visibility to label information on dropper bottle 14, speaker hole pattern 32, and translucent LED windows 34. Upper rear housing 26 preferably includes a hinge 36 for rotationally coupling with arm 38 of lever 20, a first aperture 40 for receiving a first flange 42 of lever 20, and a second aperture 44 for receiving a second flange 46 of lever 20. As shown best in FIG. 7, the internal surface 70 of upper rear housing 26 includes a structure 72 for housing an activator rod 73 and a spring 74. Activator rod 73 has an arm 76 having a pin 78 that is slidably received with a third aperture 80 on the top surface 82 of upper rear housing 26. Spring 74 biases pin 78 in an upward direction so that it extends past top surface 82. FIG. 7 shows activator rod 73 and spring 74 in both their exploded and assembled states for clarity of illustration. Lower rear surface 28 preferably includes a fourth aperture 48. Front housing 24, upper rear housing 26, and lower rear housing 28 are preferably formed from molded plastic and snap fit together. When snapped together, front housing 24 and upper rear housing 26 form a generally oval-shaped opening 50, a shelf 52 for supporting a bottom 54 of dropper bottle 14, and a first interior 56 for receiving a container 58 of bottle 14. Opening 50 and first interior 56 are designed so that they may frictionally and removably receive a dropper bottle 14 having a container 58 with either a circular or oval cross-section. As shown in the Figures, container 58 has an oval cross-section.

Plastic dropper bottle 14 preferably includes a translucent container 58, a threaded neck 60 for removably coupling with bottle closure 16, and a plug 62 frictionally secured within container 58. Plug 62 has a nozzle 64 with an aperture 66. When pressure is applied to the external surface of container 58, the fluid medicine within container 58 is expelled, as a controlled drop or a controlled stream, from aperture 66. Bottle closure 16 has internal threads (not shown) for mating with threaded neck 60 of bottle 14. Dropper bottle 14 is suitable for storing and dispensing any fluid medicine.

Device closure 18 is frictionally and removably coupled to the exterior surface of bottle closure 16. Closure 18 preferably has a bottom surface 90 and opposing wings 92. Bottom surface 90 depresses pin 78 when device closure 18 is screwed down upon bottle closure 16. Opposing wings 92 extend from the outer surface of device closure 18 to allow a patient to more easily screw closure 18 on and off bottle closure 16.

When front housing 24 and lower rear housing 28 are snapped together, a second interior 98 is created. Second interior 98 houses printed circuit board (PCB) 22. PCB 22 has a front side 100 and a rear side 102. Front side 100 preferably includes an EEPROM 104, a white high bright LED 106, a buzzer 108, a green LED 110, a Quartz X-Tal 112, a real time clock 114, a microcontroller 116, and a red LED 118. Microcontroller 116 can be any suitable microcontroller but preferably has a 80C51 architecture and is most preferably a Phillips 87LPC764 microcontroller. Green LED 110 and red LED 118 are disposed on front side 100 so as to mate with translucent LED windows 34 of front housing 24. Buzzer 108 is disposed on front side 100 so as to mate with speaker hole pattern 32 of front housing 24. High bright LED 106 is disposed on front side 100 so as to mate with an aperture 109 in shelf 52. Rear side 102 preferably includes a battery 120, a tilt switch 122, a drop counter switch 124, a device closure switch 126, a set switch 128, and a data connector 130. Battery 120 may be any suitable battery but is preferably a Lithium-3V type CR2477N battery available from Renata. Any suitable linearly activated switch may be used for switches 124, 126, and 128, but drop counter switch 124 is preferably a B3F-3122 switch available from Omron Electronics of Schaumburg, Ill.; closure switch 126 is preferably a KSM 11310 switch available from ITT Industries/Cannon of Watertown, Mass.; and set switch 128 is preferably a B3S-1000 switch available from Omron Electronics. Tilt switch 122 is preferably a 107-1007 switch available from Mouser Electronics of Mansfield, Tex. Data connector 130 may be any suitable data connector but is preferably a parallel connector. The components of printed circuit board 22 are electronically connected in the conventional manner. Drop counter switch 124 is disposed on back side 102 so as to mate with second flange 46 when flange 46 is received within second aperture 44 of upper rear housing 26. Device closure switch 126 is disposed on back side 102 so as to mate with a lower end 83 of activator rod 73. Set switch 128 is disposed on back side 102 so as to mate with fourth aperture 48 of lower rear housing 28.

Figure 10:
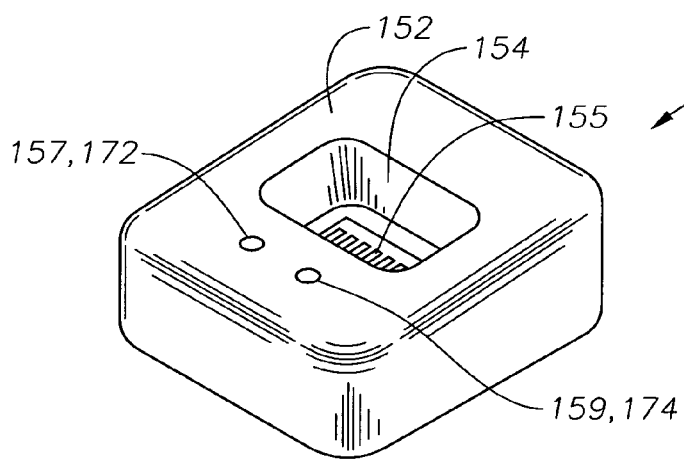
FIG. 10 shows a front, perspective view of a cradle for use with device of FIG. 1 according to a preferred embodiment of the present invention.
Figure 11:
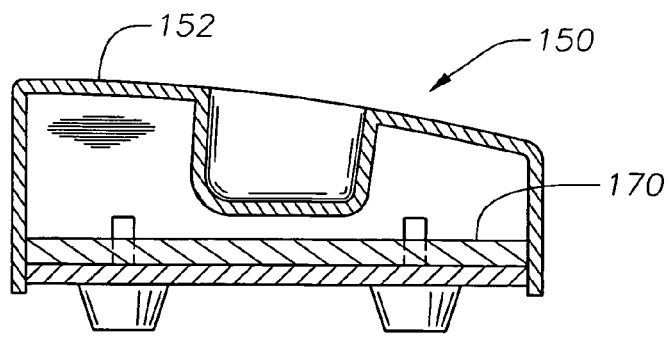
FIG. 11 shows a side, sectional view of the cradle of FIG. 10.
Figures 14, 15:
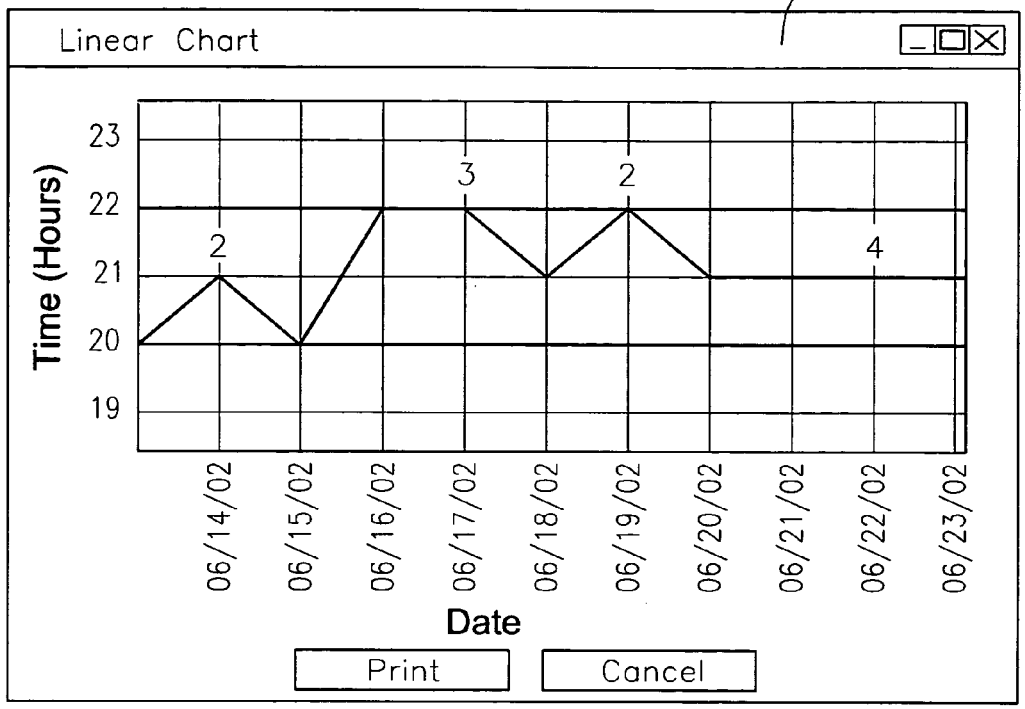
FIGS. 14–15 show exemplary reports generated from data collected from the device of FIG. 1.

FIGS. 10–12 show a cradle 150 for use with device 10 according to a preferred embodiment of the present invention. Cradle 150 has a top surface 152 having a port 154 for removably receiving a bottom surface 132 of device 10. Port 154 has a data connector 155 for operatively coupling with data connector 130 of device 10. Top surface 152 also has translucent LED windows 157 and 159. Cradle 150 also has a rear surface 156 having a data connector 158 for operatively coupling with a computer 160 via a cable 162, and a connector 164 for operatively coupling to a power source 166 via a cable 168. Data connector 155 may be any suitable data connector but is preferably a parallel data connector. Data connector 158 may be any suitable data connector but is preferably a serial data connector for operatively coupling with a data port (preferably a serial port) 167 of computer 160. Computer 160 is preferably a personal computer. Computer 160 preferably has or is operatively coupled to both a display 163 and a user interface 165. Display 163 preferably has touch screen capability. User interface 165 preferably includes a keyboard and a computer mouse. Computer 160 is preferably loaded with software that enables a physician or his or her staff to program device 10 and to obtain and display data from device 10. This software is preferably Windows®-based software and is most preferably Visual Basic available from Microsoft. Connector 164 is preferably an AC power connector. Power source 166 is preferably an AC power source, such as a conventional wall socket. The various electrical components of cradle 150 are mounted on and electronically connected via a printed circuit board ("PCB") 170 in the conventional manner. PCB 170 has a red LED 172 disposed under LED window 157 and a green LED 174 disposed under LED window 159. Device 10, cradle 150, and computer 160 may electronically communicate via any suitable protocol. The preferred communication protocol is I2C.

The operation and use of device 10 and cradle 150 according to a preferred method of the present invention will now be described in greater detail. Cradle 150 is operatively coupled to computer 160 and power source 166 as described above. When power is being supplied to cradle 150, red LED 172 will be on. Device 10 is placed within port 154 of cradle 150 so that data connector 130 of device 10 is operatively coupled to data connector 155 of cradle 10. When data connector 130 is operatively coupled to data connector 155, green LED 174 will be on. If data connector 130 is not operatively coupled to data connector 135, green LED 174 will be off. Using the software loaded on computer 160, display 163, and user interface 165, a physician or his or her staff may load a particular patient's information (e.g. patient identification number, first name, last name, sex, date of birth) from computer 160 to device 10, or from device 10 to computer 160. All such information is stored in EEPROM 104 in device 10. A physician or his or her staff may similarly load the correct date and time from computer 160 to real time clock 114 of device 10. A physician or his or her staff may customize the device parameters for a particular patient (e.g. number of drops, next medication time (hours:minutes), number of reminders, buzzer number, dosage window (hours), tolerance window (hours), dosage interval (hours), reminder interval (minutes), device closure off (seconds)) for device 10 using computer 160, display 163, and user interface 165. FIG. 13 shows an exemplary screen 176 showing patient information and device parameters suitable for display 163 of computer 160. The next medication time parameter is preferably used for medicines that require only once per day dosing. The dosage interval parameter is preferably used for medicines with dosage intervals of more than once per day. The software on computer 160 will only allow a physician to program either the next medication time parameter or the dosage interval parameter, but not both parameters. After customization, the parameters on screen 176 may be transferred to EEPROM 104 of device 10 using touch screen button 178. It should be noted that the patient identification number, the number of drops parameter, the next medication time parameter, and the dosage interval parameter preferably may only be modified when device 10 is properly positioned within port 154 of cradle 150 so that device 10 and computer 160 are in electronic communication. This insures that device 10 always has the current information for these parameters. All other parameters can be customized "offline" when device 10 and computer 160 are not in electronic communication. During any data transfer between device 10 and computer 160, green LED 174 of cradle 150 will blink. Although not shown on FIG. 13, screen 176 may not include the number of drops parameter and device 10 may be manufactured to assume a fixed number of drops, such as one drop.

When device 10 is positioned within port 154 of cradle 150 so that device 10 and computer 160 are in electronic communication, medicine dosing data (e.g. number of drops of fluid medicine dispensed, date and time of dispensing of fluid medicine) for a particular patient is automatically transferred from EEPROM 104 of device 10 to personal computer 160. A physician or his or her staff may review and analyze such data for a particular patient via touch screen buttons 180 and 182 of screen 176. When touch screen button 180 is depressed, a linear chart showing medicine dosing data for a particular patient is shown on display 163. An exemplary linear chart is shown in screen 184 of FIG. 14. The bolded lines represent the tolerance window parameter. A number by a certain data point shows the specific number of drops dispensed only when more or fewer drops than specified by the current value of the number of drops parameter stored in EEPROM 104 were actually dispensed. When touch screen button 182 is depressed, a drop log showing medicine dosing data for a particular patient is shown on display 163. An exemplary drop log is shown in screen 186 of FIG. 15.

Once device 10 has been properly programmed by a physician or his or her staff, it is ready for use by a patient. Device 10 is portable and can be used by a patient wherever convenient. When microcontroller 116 determines that it is time for a patient to take his or her medicine (as determined by the value of the next medication time parameter stored in EEPROM 104 and the current time provided by real time clock 114), microcontroller 116 causes buzzer 108 to emit short beeps and causes green LED 110 to blink. The number of beeps and blinks will be consistent with the current value of the buzzer number parameter in EEPROM 104. If the patient does not take his or her medicine within the time period defined by the current value of the reminder interval parameter in EEPROM 104, microcontroller 116 once again causes buzzer 108 to emit short beeps and green light LED 110 to blink. If the patient continues to not take his or her medicine, device 10 will continue to remind the patient, as described above, for the number of reminders indicated by the current value of the number of reminders parameter stored in EEPROM 104.

When the patient is alerted to take medicine, he or she screws device closure 18, and simultaneously bottle closure 16, off threaded neck 60, allowing spring 74 to move activator rod 73 upward so that end 83 of actuator rod 73 no longer contacts device closure switch 126. Switch 126 signals microcontroller 116 to activate the medicine dispensing recording mode of device 10 and to turn high bright LED 106 on.

The patient then orients device 10 so that aperture 66 of nozzle 64 is above his or her eye and container 58 is generally above nozzle 64. Light from high bright LED 106 shines through translucent container 58 and is visible to the patient through aperture 66 to help the patient properly align nozzle 64 over his or her eye. When device 10 is so oriented, tilt switch 122 signals microcontroller 116. The patient then presses lever 20 the appropriate number of times to dispense the appropriate amount of medicine into each eye. Each time lever 20 is depressed, first flange 42 preferably contacts container 58 with the appropriate amount of pressure to dispense a controlled drop of fluid medicine from aperture 66. Alternatively, device 10 may be designed so that each time lever 20 is depressed, first flange 42 preferably contacts container 58 with the appropriate amount of pressure to dispense a controlled stream of fluid medicine from aperture 66. In addition, each time lever 20 is depressed, second flange 46 contacts drop counter switch 124. Assuming device closure switch 126 has signaled microcontroller 116 to activate the medicine dispensing recording mode of device 10 and tilt switch 122 has signaled microcontroller 116 that device 10 is properly oriented to dispense medication, microcontroller 116 records each drop dispensed to EEPROM 104 as indicated by drop counter switch 124. Microcontroller 116 also causes the date and time of each drop dispensed, as provided by real time clock 114, to be recorded to EEPROM 104. Microcontroller 116 further causes buzzer 108 to emit one short beep to signify to the patient that proper dispensing of a drop has been recorded. If device closure switch 126 has not signaled microcontroller 116 to activate the medicine dispensing recording mode of device 10 or tilt switch 122 has not signaled microcontroller 116 that device 10 is properly oriented to dispense medication, then the depression of lever 20 is considered to be inadvertent and the dispensing of a drop is not recorded by EEPROM 104.

After dispensing the medication, the user screws device closure 18 and bottle closure 16 on threaded neck 60. With device closure 18 and bottle closure 16 appropriately placed on neck 60, device closure 18 depresses pin 78, activator rod 73 is moved downward, and device closure switch 126 signals microcontroller 116 to deactivate the medicine dispensing recording mode of device 10 and to turn high bright 106 off. If the patient forgets to replace device closure 18 within the time period of the current value of the device closure off parameter in EEPROM 104, microcontroller 116 causes buzzer 108 to emit long beeps and causes red LED 118 to blink. If the patient does not replace device closure 18 within the time period defined by the current value of the reminder interval parameter in EEPROM 104, microcontroller 116 once again causes buzzer 108 to emit long beeps and causes red LED 118 to blink. The number of beeps and blinks will be consistent with the current value of the buzzer number parameter in EEPROM 104. If the patient continues to not replace device closure 18, device 10 will continue to remind the patient, as described above, for the number of reminders indicated by the current value of the number of reminders parameter stored in EEPROM 104.

The medicine dispensing process, as described above, is repeated again when microcontroller 116 next determines that it is time to notify the patient to take his or her medicine. If device 10 determines that the patient properly dispenses drops into the eye within 12 hours of the next time to take medicine, as described above, microcontroller 116 cancels the next medication time parameter for the next dosage.

Device 10 preferably allows the patient to change the next medication time parameter stored in EEPROM 104, but only if the physician has initially programmed device 10 to operate with the next medication time parameter (versus the dosage interval parameter). The patient may desire to change this time if, by way of example, it begins to conflict with his or her daily schedule. To change the next medication time parameter, the patient may introduce the end of a paper clip, or similar object, into aperture 48 so as to depress set switch 128 for four continuous seconds. After the initial four second depression, switch 128 may be held down, or pressed repeatedly, to increase the next time to take medication parameter in one minute increments. When the patient ceases depressing switch 128 for four seconds, the next medication time parameter is set, and microcontroller 116 causes buzzer 108 to emit a long beep to indicate that the parameter has been successfully changed.

From the above, it may be appreciated that the present invention provides the patient and physician with an improved device for dispensing fluid medicines from both physiological and compliance perspectives. The device maximizes patient safety and ease of use, and does not suffer from the limitations of existing devices.

The present invention is illustrated herein by example, and various modifications may be made by a person of ordinary skill in the art. For example, although the preferred operation of the device has been described above in connection with dispensing fluid medicine to the eye, the device may be used to dispense fluid medicine topically to other portions of the body such as the skin, ears, or nose. As another example, although the preferred programming and operation of the device has been described above in connection with the next medication time parameter of screen 176 of FIG. 13, the dosage interval parameter of screen 176 may be used in lieu of the next medication time parameter for medicines with dosage intervals of more than once per day.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A dispensing device for fluid medicine, comprising:
   a housing having an opening leading to an interior;
   a plastic dropper bottle at least partially disposed in said interior through said opening, said bottle having a container holding fluid medicine to be dispensed and a nozzle with an aperture in fluid communication with said container; and
   a printed circuit board disposed within said housing and having a microcontroller and a switch in electrical communication with said microcontroller, wherein said switch signals said microcontroller when said device is oriented by a user so that said container is disposed generally above said nozzle.

2. A dispensing device for fluid medicine, comprising:
   a housing having an opening leading to an interior;
   a plastic dropper bottle at least partially disposed in said interior through said opening, said bottle having a container holding fluid medicine to be dispensed and a nozzle with an aperture in fluid communication with said container;
   a closure; and
   a printed circuit board disposed within said housing and having a microcontroller and a switch in electrical communication with said microcontroller, said switch sensing whether said closure is disposed on said device;
   wherein said microcontroller activates a medicine dispensing recording mode of said device when said switch signals said microcontroller that said closure is not disposed on said device.

* * * * *